US008202329B2

(12) United States Patent
Murphy et al.

(10) Patent No.: US 8,202,329 B2
(45) Date of Patent: Jun. 19, 2012

(54) TRIACYLGLYCEROL-BASED ALTERNATIVE TO PARAFFIN WAX

(75) Inventors: Timothy A. Murphy, Derby, KS (US); Melinda Kae Doucette, Wichita, KS (US); Nathaniel C. House, III, Fayetteville, NC (US); Michael L. Richards, Cedar Rapids, IA (US)

(73) Assignee: Elevance Renewable Sciences, Inc., Woodbridge, IL (US)

( * ) Notice: Subject to any disclaimer, the term of this patent is extended or adjusted under 35 U.S.C. 154(b) by 1270 days.

(21) Appl. No.: 11/801,851

(22) Filed: May 11, 2007

(65) Prior Publication Data

US 2007/0282000 A1 Dec. 6, 2007

Related U.S. Application Data

(63) Continuation of application No. 10/655,945, filed on Sep. 5, 2003, now Pat. No. 7,217,301, which is a continuation of application No. 09/877,716, filed on Jun. 8, 2001, now Pat. No. 6,645,261, which is a continuation-in-part of application No. 09/543,929, filed on Apr. 6, 2000, now abandoned, and a continuation-in-part of application No. 09/519,812, filed on Mar. 6, 2000, now abandoned.

(51) Int. Cl.
*C10L 1/18* (2006.01)
*A61K 8/02* (2006.01)

(52) U.S. Cl. ............................ 44/308; 424/401; 44/275

(58) Field of Classification Search .................... 44/275, 44/308; 424/401

See application file for complete search history.

(56) References Cited

U.S. PATENT DOCUMENTS

| | | | | |
|---|---|---|---|---|
| 1,935,946 | A | 11/1933 | Egan et al. | |
| 1,954,659 | A | 4/1934 | Will | |
| 2,294,229 | A * | 8/1942 | Fiero | 424/670 |
| 2,468,799 | A * | 5/1949 | Ziels et al. | 554/147 |
| 2,784,891 | A | 3/1957 | Thielke | |
| 3,448,178 | A | 6/1969 | Flanagan | |
| 3,630,697 | A | 12/1971 | Duling et al. | |
| 3,645,705 | A | 2/1972 | Miller et al. | |
| 3,744,956 | A | 7/1973 | Hess | |
| 3,844,706 | A | 10/1974 | Tsaras | |
| 4,118,203 | A | 10/1978 | Beardmore et al. | |
| 4,134,718 | A | 1/1979 | Kayfetz et al. | |
| 4,292,088 | A | 9/1981 | Scheuffgen et al. | |
| 4,293,345 | A | 10/1981 | Zeilstra et al. | |
| 4,314,915 | A | 2/1982 | Wiegers et al. | |
| 4,390,590 | A | 6/1983 | Saunders et al. | |
| 4,411,829 | A | 10/1983 | Schulte-Elte et al. | |
| 4,434,306 | A | 2/1984 | Kobayashi et al. | |
| 4,507,077 | A | 3/1985 | Sapper | |
| 4,545,941 | A | 10/1985 | Rosenburg | |
| 4,554,107 | A | 11/1985 | Takao | |
| 4,567,548 | A | 1/1986 | Schneeberger | |
| 4,608,011 | A | 8/1986 | Comstock | |
| 4,614,625 | A | 9/1986 | Wilson | |
| 4,623,488 | A | 11/1986 | Takao | |
| 4,714,496 | A | 12/1987 | Luken, Jr. et al. | |
| 4,759,709 | A | 7/1988 | Luken, Jr. et al. | |
| 4,813,975 | A | 3/1989 | Poulina et al. | |
| 4,842,648 | A | 6/1989 | Phadoemchit et al. | |
| 4,855,098 | A | 8/1989 | Taylor | |
| 4,923,708 | A | 5/1990 | Given, Jr. | |
| 5,171,329 | A | 12/1992 | Lin | |
| 5,258,197 | A | 11/1993 | Wheeler et al. | |
| 5,338,187 | A | 8/1994 | Elharar | |
| 5,380,544 | A | 1/1995 | Kiemann et al. | |
| 5,578,089 | A | 11/1996 | Elsamaloty | |
| 5,660,865 | A | 8/1997 | Pedersen et al. | |
| 5,700,516 | A | 12/1997 | Sandvick et al. | |
| 5,723,137 | A | 3/1998 | Wahle et al. | |
| 5,753,015 | A * | 5/1998 | Sinwald et al. | 106/31.34 |
| 5,843,194 | A | 12/1998 | Spaulding | |
| 5,885,600 | A | 3/1999 | Blum et al. | |
| 5,888,487 | A | 3/1999 | Baumoeller et al. | |
| 6,001,286 | A | 12/1999 | Sleeter | |
| 6,019,804 | A | 2/2000 | Requejo et al. | |
| 6,022,402 | A | 2/2000 | Stephenson et al. | |

(Continued)

FOREIGN PATENT DOCUMENTS

DE 19956226 A1 5/2001

(Continued)

OTHER PUBLICATIONS

Oliefabrik et al., "Paper coating", *Research Disclosure Journal*, Dec. 1996 (2 pgs.).
Abstract of EP 536861 A1, "Wrapping paper for fatty foodstuff of good biodegradability-having surface treated with hydrogenated animal or vegetable fat", *Derwent World Patents Index*, available at http://toolkit.dialog.com/intranet/cgi/present, Publication Date Apr. 14, 1993 (2 pgs.).
Japanese Abstract of JP 56032550 A, "Coating compsn. for paper bags protecting fruit on trees—comprises hydrogenated oil and/or solid natural fat with was, e.g. paraffin", *Derwent World Patents Index*, available at http://www.dialogclassic.com/main.vmgw, Publication Date Apr. 2, 1981 (1 pg.).
European Abstract of EP 811664 A1, "Coating compositions for e.g. foodstuffs—contg mono and di glyceride(s) and colophony ester(s)", *Derwent World Patents Index*, available at http://toolkit.dialog.com/intranet/cgi/present, Publication Date Dec. 10, 1997 (1 pg.).

(Continued)

*Primary Examiner* — Cephia D Toomer
(74) *Attorney, Agent, or Firm* — Brinks Hofer Gilson & Lione

(57) ABSTRACT

A triacylglycerol-based wax, which can be used in candle making, is provided. The triacylglycerol-based material is predominantly includes a triacylglycerol stock which has a fatty acid profile has no more than about 25 wt. % fatty acids having less than 18 carbon atoms. In addition, the fatty acid profile of the triacylglycerol typically includes at least about 50 wt. % 18:1 fatty acid and no more than about 25 wt. % 18:0 fatty acid. In another embodiment, the triacylglycerol-based material is characterized in part by an Iodine Value of about 60 to about 75. For applications such as candles, the wax commonly includes a hydrogenated vegetable oil and palmitic acid. Candles formed from triacylglycerol-based material and methods of producing the candles are also provided.

26 Claims, No Drawings

U.S. PATENT DOCUMENTS

| | | | |
|---|---|---|---|
| 6,063,144 | A | 5/2000 | Calzada et al. |
| 6,099,877 | A | 8/2000 | Schuppan |
| 6,103,308 | A | 8/2000 | Floyd et al. |
| 6,106,597 | A | 8/2000 | Starks et al. |
| 6,123,979 | A | 9/2000 | Hepburn et al. |
| 6,127,326 | A | 10/2000 | Dieckmann et al. |
| 6,132,742 | A | 10/2000 | Le Bras et al. |
| 6,156,369 | A | 12/2000 | Eger et al. |
| 6,201,053 | B1 | 3/2001 | Dieckmann et al. |
| 6,214,918 | B1 | 4/2001 | Johnson et al. |
| 6,224,641 | B1 | 5/2001 | Matzat et al. |
| 6,238,926 | B1 | 5/2001 | Liu et al. |
| 6,255,375 | B1 | 7/2001 | Michelman |
| 6,258,965 | B1 | 7/2001 | O'Lenick, Jr. |
| 6,262,153 | B1 | 7/2001 | Webster et al. |
| 6,276,925 | B1 | 8/2001 | Varga |
| 6,277,310 | B1 | 8/2001 | Sleeter |
| 6,284,007 | B1 | 9/2001 | Tao |
| 6,497,735 | B2 | 12/2002 | Tao |
| 6,503,077 | B2 | 1/2003 | Orth et al. |
| 6,503,285 | B1 | 1/2003 | Murphy |
| 6,582,728 | B1 | 6/2003 | Platz et al. |
| 6,582,748 | B1 | 6/2003 | Loh et al. |
| 6,586,506 | B2 | 7/2003 | Webster et al. |
| 6,599,334 | B1 | 7/2003 | Anderson |
| 6,645,261 | B2 | 11/2003 | Murphy et al. |
| 6,673,763 | B1 | 1/2004 | Hansen et al. |
| 6,730,137 | B2 | 5/2004 | Pesu et al. |
| 6,733,548 | B2 | 5/2004 | Rasmussen et al. |
| 6,758,869 | B2 | 7/2004 | Roeske et al. |
| 6,770,104 | B2 | 8/2004 | Murphy |
| 6,773,469 | B2 | 8/2004 | Murphy |
| 6,797,020 | B2 | 9/2004 | Murphy |
| 6,824,572 | B2 | 11/2004 | Murphy |
| 6,846,573 | B2 | 1/2005 | Seydel |
| 6,852,140 | B1 | 2/2005 | Roeske |
| 6,943,262 | B2 | 9/2005 | Kodali et al. |
| 7,037,439 | B2 | 5/2006 | Tavares |
| 7,128,766 | B2 | 10/2006 | Murphy et al. |
| 7,176,171 | B2 | 2/2007 | Nieendick et al. |
| 7,192,457 | B2 | 3/2007 | Murphy et al. |
| 7,217,301 | B2 | 5/2007 | Murphy et al. |
| 7,387,649 | B2 | 6/2008 | Tao |
| 7,462,205 | B2 | 12/2008 | Murphy |
| 7,510,584 | B2 | 3/2009 | Cap |
| 7,569,084 | B2 | 8/2009 | Tao et al. |
| 7,588,607 | B1 | 9/2009 | Cap |
| 7,601,184 | B2 | 10/2009 | Tischendorf |
| 7,629,479 | B2 | 12/2009 | Kondo et al. |
| 7,637,968 | B2 | 12/2009 | Murphy |
| 7,833,294 | B2 | 11/2010 | Murphy et al. |
| 2001/0013195 | A1 | 8/2001 | Tao |
| 2001/0051680 | A1 | 12/2001 | Webster et al. |
| 2002/0005007 | A1 | 1/2002 | Roeske et al. |
| 2002/0144455 | A1 | 10/2002 | Bertrand et al. |
| 2002/0157303 | A1 | 10/2002 | Murphy et al. |
| 2003/0008257 | A1 | 1/2003 | Tao |
| 2003/0017431 | A1 | 1/2003 | Murphy |
| 2003/0022121 | A1 | 1/2003 | Biggs |
| 2003/0046860 | A1 | 3/2003 | Tiffany et al. |
| 2003/0057599 | A1 | 3/2003 | Murphy et al. |
| 2003/0061760 | A1 | 4/2003 | Tao et al. |
| 2003/0091949 | A1 | 5/2003 | Pesu et al. |
| 2003/0110683 | A1 | 6/2003 | Murphy |
| 2003/0134244 | A1 | 7/2003 | Gray et al. |
| 2003/0176300 | A1 | 9/2003 | Kodali et al. |
| 2003/0198826 | A1 | 10/2003 | Seydel |
| 2003/0207971 | A1 | 11/2003 | Stuart, Jr. et al. |
| 2003/0213163 | A1 | 11/2003 | Berger et al. |
| 2004/0000088 | A1 | 1/2004 | Wesley |
| 2004/0037859 | A1 | 2/2004 | Cecchi et al. |
| 2004/0047886 | A1 | 3/2004 | Murphy et al. |
| 2004/0076732 | A1 | 4/2004 | Valix |
| 2004/0088907 | A1 | 5/2004 | Murphy |
| 2004/0088908 | A1 | 5/2004 | Murphy |
| 2004/0138359 | A1 | 7/2004 | Dinkelaker et al. |
| 2004/0200136 | A1 | 10/2004 | Tao et al. |
| 2004/0221503 | A1 | 11/2004 | Murphy et al. |
| 2004/0221504 | A1 | 11/2004 | Murphy |
| 2004/0250464 | A1 | 12/2004 | Rasmussen et al. |
| 2005/0014664 | A1 | 1/2005 | Nadolsky et al. |
| 2005/0060927 | A1 | 3/2005 | Murphy |
| 2005/0095545 | A1 | 5/2005 | Tischendorf |
| 2005/0123780 | A1 | 6/2005 | Seydel |
| 2005/0158679 | A1 | 7/2005 | Chen et al. |
| 2005/0269728 | A1 | 12/2005 | Roos |
| 2006/0236593 | A1 | 10/2006 | Cap |
| 2006/0272199 | A1 | 12/2006 | Licciardello et al. |
| 2006/0272200 | A1 | 12/2006 | Murphy et al. |
| 2007/0006521 | A1 | 1/2007 | Licciardello et al. |
| 2007/0006522 | A1 | 1/2007 | Tao |
| 2007/0056211 | A1 | 3/2007 | Li et al. |
| 2007/0144058 | A1 | 6/2007 | Chen et al. |
| 2007/0151480 | A1 | 7/2007 | Bloom et al. |
| 2007/0270621 | A1 | 11/2007 | Millis et al. |
| 2008/0027194 | A1 | 1/2008 | Schrodi |
| 2008/0064891 | A1 | 3/2008 | Lee |
| 2008/0138753 | A1 | 6/2008 | Tao et al. |
| 2008/0145808 | A1 | 6/2008 | Lee |
| 2008/0206411 | A1 | 8/2008 | Nielsen |
| 2008/0307696 | A1 | 12/2008 | Wu et al. |
| 2009/0048459 | A1 | 2/2009 | Tupy et al. |
| 2009/0119977 | A1 | 5/2009 | Murphy |
| 2009/0217568 | A1 | 9/2009 | Murphy et al. |
| 2009/0259065 | A1 | 10/2009 | Abraham et al. |
| 2009/0264672 | A1 | 10/2009 | Abraham et al. |
| 2010/0024281 | A1 | 2/2010 | Lemke et al. |
| 2010/0044924 | A1 | 2/2010 | Cap |
| 2010/0047499 | A1 | 2/2010 | Braksmayer et al. |
| 2010/0132250 | A1 | 6/2010 | Uptain et al. |
| 2010/0145086 | A1 | 6/2010 | Schrodi et al. |
| 2010/0205851 | A1 | 8/2010 | Uptain et al. |

FOREIGN PATENT DOCUMENTS

| | | | |
|---|---|---|---|
| EP | 0429995 | A2 * | 6/1991 |
| EP | 0536861 | A1 | 4/1993 |
| EP | 0545715 | A1 | 6/1993 |
| EP | 0 685 554 | A1 | 12/1995 |
| EP | 0811664 | A1 | 12/1997 |
| EP | 1693436 | A1 | 8/2006 |
| EP | 1696022 | A1 | 8/2006 |
| EP | 1801096 | A1 | 6/2007 |
| JP | 56-32550 | A | 4/1981 |
| JP | 4059897 | A2 | 2/1992 |
| JP | 6009987 | A | 1/1994 |
| JP | 09-014574 | A | 1/1997 |
| WO | WO 92/00269 | A1 | 1/1992 |
| WO | WO 96/00815 | A1 | 1/1996 |
| WO | WO 96/14373 | A1 | 5/1996 |
| WO | WO 98/45390 | A1 | 10/1998 |
| WO | WO 99/27043 | A1 | 6/1999 |
| WO | WO 02/30386 | A1 | 4/2002 |
| WO | WO 02/092736 | A1 | 11/2002 |
| WO | WO 03/012016 | A1 | 2/2003 |
| WO | WO 03/051134 | A2 | 6/2003 |
| WO | WO 03/057983 | A1 | 7/2003 |
| WO | WO 03/104348 | A1 | 12/2003 |
| WO | WO 2004/033388 | A1 | 4/2004 |
| WO | WO 2004/083310 | A1 | 9/2004 |
| WO | WO 2004/101720 | A1 | 11/2004 |
| WO | WO 2005/042655 | A1 | 5/2005 |
| WO | WO 2006/041011 | A1 | 4/2006 |
| WO | WO 2006/076364 | A2 | 7/2006 |
| WO | WO 2007/002999 | A1 | 1/2007 |
| WO | WO 2008/008420 | A1 | 1/2008 |
| WO | WO 2008/010961 | A2 | 1/2008 |
| WO | WO 2008/048520 | A2 | 4/2008 |
| WO | WO 2008/103289 | A1 | 8/2008 |
| WO | WO 2008/140468 | A2 | 11/2008 |
| WO | WO 2008/151064 | A1 | 12/2008 |
| WO | WO 2008/157436 | A1 | 12/2008 |

OTHER PUBLICATIONS

Behren et al., "Beeswax and other Non-Paraffin Waxes," Presented at NCA Technical Meeting, Jun. 19-20, 1991, 6 pages.

Bell et al., "Sperm Oil Replacements: Synthetic Wax Esters from Selectively Hydrogenated Soybean and Linseed Oils," *Journal of the American Oil Chemists' Society*, Jun. 1977, pp. 259-263, vol. 54.
Pages from Bitter Creek Candle Supply, Inc., Website (http://www.execpc.com.~bcsupply; now @ http://www.candlesupply.com), available at least by Jun. 29, 2000, 9 pages.
Pages from Ecowax, Nature's Gifts, Inc., Website (http://ngiwax.com/ecowax.htm), available at least by Jul. 5, 2000, 3 pages.
Pages from Heartland Candleworks Website, available @ www.candleworks.org, available at least by Feb. 11, 2000, 4 pages.
Frahm, "Harvest Lights: The only soy-based candle, a bright idea," available @ http://www.extension.uiuc.edu/~stratsoy/new/news/html/909166253,html, Oct. 23, 1998, 2 pages.
*In Business* "America's Shining Example of Sustainable Business," available @ http://www.candleworks.org, Mar./Apr. 1998, 3 pages.
Noller, Chemistry of Organic Compounds, W.B. Saunders Company, 1957, pp. 181 and 192.
Orso, "New Use for Soybeans Has Bright Future," available @ http://www.unitedsoybean.com/news/nr981014.htm, Oct. 14, 1998, 2 pages.
Purdue Agriculture News, Purdue May Agriculture & Natural Resources Package, available @ http://purduenews.uns.purdue.edu/UNS/paks/agpak.digest.9605.html, May 1996, 3 pages.
Purdue News, "Purdue students put the 'happy' back into birthday candles," available @ http://www.purdue.edu/UNS/html4ever/9611.Schweitzer.candles.html, Nov. 1996, 3 pages.
Purdue News, "Purdue students put the 'happy' back into birthday candles," available @ http:/www.purdue.edu/UNS/html4ever/9604.schweitzer.html, May 1996, 2 pages.
Purdue University School of Agriculture, 1998 Farm Progress Show, available @ http://www.admin.ces.purdue.edu/anr/98fps/fpspix/930.html, 1998, 4 pages.
Tao, "Development of Vegetable Lipid-Based Candles," available at http://abe.www.ecn.purdue.edu/ABE/Research/research94/REPORT.94.Book_68.html, 1994, 2 pages.
Erhan et al. , "Drying Properties of Metathesized Soybean Oil," Journal of American Oil Chemists' Society, AOCS Press, vol. 74, No. 6, 1997, pp. 703-706.
Mol, "Applications of Olefin Metathesis in Oleochemistry: An Example of Green Chemistry," Green Chemistry, Royal Society of Chemistry, Cambridge, GB, vol. 4, 2002, pp. 5-13.
Rezaei, "Hydrogenated Vegetable Oils as Candle Wax," J. of the Am. Oil Chemists' Society, vol. 12, No. 79, pp. 1241-1247 (Dec. 2002).

* cited by examiner

TRIACYLGLYCEROL-BASED ALTERNATIVE TO PARAFFIN WAX

CROSS REFERENCE TO RELATED APPLICATIONS

This application is a continuation of U.S. patent application Ser. No. 10/655,945 which is a continuation of U.S. patent application Ser. No. 09/877,716 (filed Jun. 8, 2001), now U.S. Pat. No. 6,645,261, which is a continuation-in-part of U.S. patent application Ser. No. 09/519,812 (filed Mar. 6, 2000) and a continuation-in-part of U.S. patent application Ser. No. 09/543,929 (filed Apr. 6, 2000), the complete disclosures of which are incorporated herein by reference.

BACKGROUND

Candles have been known and used for illumination since early civilization. For years, beeswax was has been in common usage as a natural wax for candles, cosmetics and sealing waxes for food preservation. A typical candle is formed of a solid or semi-solid body of combustible waxy material, such as paraffin wax or beeswax, and contains an combustible fibrous wick embedded within the waxy material. When the wick of a candle is lit, the generated heat melts the solid wax, and the resulting liquid flows up the wick by capillary action and is combusted. At present, although many advanced illuminating devices are available, candles are still popularly used for decoration or on a special situation as a holiday.

Over one hundred years ago, paraffin came into existence, parallel with the development of the petroleum refining industry. Paraffin was introduced as a bountiful and low cost alternative to beeswax which has become more and more costly and in more and more scarce supply. Paraffin is simply the leftover residue from refining gasoline and motor oils. Paraffin is presently the primary industrial wax for the following three uses: candles, cosmetics and sealing waxes.

Conventional candles are made from a wax material, such as paraffin. Such candles typically emit a smoke and can produce a bad smell when burning. Many people can not accept such smell. In addition, a small amount of particles ("particulates") are often created when the candle burns. These particles may affect the health of a human when breathed in. Paraffin soot particles are similar to particles given off by burning diesel fuel, which include a number of polycyclic aromatic hydrocarbons that have been deemed toxic air contaminants.

In addition to these issues, paraffin wax is diminishing in supply as consumer demand increases. New petroleum technology does not produce by-product petro-waxes. This decrease in supply requires importation of petroleum waxes. This coincides with a huge ($2.5 billion) decorative candle market in the U.S. that is growing at about 15% per year.

There is a strong consumer need and demand for alternative natural waxes as an option to toxic paraffin waxes that can be produced at a rate that is cost competitive with toxic paraffin. Accordingly, it would be advantageous to have other materials which can be used to form clean burning base materials for forming candles. If possible, such materials would preferably be biodegradable and be derived from renewable raw materials. The candle base materials should preferably have physical characteristics, e.g., in terms of melting point, hardness and/or malleability, that permit the material to be readily formed into candles having a pleasing appearance and/or feel to the touch, as well as having desirable olfactory properties.

SUMMARY

The fatty acid profile of the triacylglycerol stock which makes up the predominant portion of the present triacylglycerol-based material generally consists predominantly of fatty acids having 18 carbon atoms. The content of shorter chain fatty acids, i.e., fatty acids having 16 carbon atoms or less, in the fatty acid profile of the triacylglycerols is generally no more than about 25 wt. %. The triacylglycerol stock typically has a fatty acid profile including no more than about 25 wt. % fatty acids having less than 18 carbon atoms.

One embodiment of the present invention relates to candles having low paraffin content and methods of producing such candles. The candles are formed from triacylglycerol-based material, a biodegradable material produced from renewable resources. Since the candles are formed from a material with a low paraffin content and preferably are substantially devoid of paraffin, the candles are clean burning, emitting very little soot. The combination of low soot emission, biodegradability and production from renewable raw material makes the present candle a particularly environmentally friendly product.

The candles may be made from pure triacylglycerol or may include minor amounts of other additives to modify the properties of the waxy material. Examples of types of additives which may commonly be incorporated into the present candles include colorants, fragrances, insect repellants, and the like.

Another embodiment of the present invention is a vegetable-based wax comprising up to 100% hydrogenated vegetable oil. Vegetable-based waxes can be formulated to replace petroleum-based waxes used in various applications. For example, candles, cosmetics, or food wrapper coatings. These vegetable-based waxes are non-toxic. For some applications, the vegetable-based waxes have superior properties to the petroleum-based products. The vegetable oil waxes, particularly the hydrogenated soybean oil based wax, of the present invention are cost competitive with paraffin in addition to being non-toxic.

The triacylglycerol-based materials used to form the present candles are semi-solid or solid, firm but not brittle, generally somewhat malleable, with no free oil visible. Such materials typically are formed predominantly from a triacylglycerol stock having a solid fat content of no higher than about 20% at 40° C. (104° F.). The triacylglycerol stock typically is chosen to have a melting point of about 40° C. to 45° C.

In another embodiment of the invention, the melting characteristics of the triacylglycerol-based material may be controlled based on its solid fat index. The solid fat index is a measurement of the solid content of a triacylglycerol material as a function of temperature, generally determined at number of temperatures over a range from 10° C. (50° F.) to 40° C. (104° F.). For simplicity, the triacylglycerol-based materials described herein can be characterized in terms of their solid fat index at 10° C. ("S FI-10") and/or 40° C. ("SFI-40"). Suitable triacylglycerol stock for use in making the present candles have a solid fat index exemplified by a solid fat content at 10° C. ("S FI-10") of about 40-60 wt. % and solid fat index at 40° C. ("S FI-40") of about 2-15 wt. %.

The triacylglycerol-based material generally includes triacylglycerol having a fatty acid profile which typically includes no more than about 25 wt. % fatty acids having less than 18 carbon atoms. In addition, the fatty acid profile of the triacylglycerol typically includes at least about 50 wt. % 18:1 fatty acid and no more than about 20 wt. % 18:0 fatty acid ("stearic acid"). A triacylglycerol stock may also be characterized by its Iodine Value. The triacylglycerol stock used to produce the candles typically have an Iodine Value of about 60 to about 75.

The present application also provides candle beads formed from the triacylglycerol-based material and methods of producing candles using the triacylglycerol-based material.

DETAILED DESCRIPTION

Generally, the wax of the present invention is used in applications like the waxes which it replaces. However, some considerations must be taken into account. The waxes of the present invention are generally processed at lower temperatures than a corresponding petroleum-based wax. This lower energy input is advantageous to cost considerations and may avoid effects such as discoloration of the wax. The wax of the present invention generally burns at a lower temperature than petroleum-based waxes as well. This can be an advantage for an application such as aromatherapy candles. In such an application, the oils can be better able to volatilize without problems such as oxidation.

In one embodiment, the wax of the present invention comprises hydrogenated vegetable oil. Soybean oil is the preferred vegetable oil, but other oils can be used, such as corn, cotton, palm, olive, canola, and the like. Generally, the invention is expected to work for any fatty acids from oil seeds. One of ordinary skill in the art would be able to determine other plant oils which will work. It is expected that combinations of vegetable oils will work as well.

The level of hydrogenation of the oil varies with the end use application. The level of hydrogenation can be correlated with the desired characteristics of the wax. Since hydrogenation solidifies oils, for softer waxes, less hydrogenation is necessary, and for more solid waxes, more hydrogenation is used. The level of hydrogenation may be varied for aesthetic as well as functional purposes. The preferred level of hydrogenation is about 60% to about 100%. One of ordinary skill in the art would be able to determine the level of hydrogenation for a particular application. Combinations of vegetable oils hydrogenated to different levels can be used to achieve a desired application.

Suitable hydrogenated vegetable oils for use in the present triacylglycerol-based material includes hydrogenated soybean oil, hydrogenated cottonseed oil, hydrogenated sunflower oil, hydrogenated canola oil, hydrogenated corn oil, hydrogenated olive oil, hydrogenated peanut oil, hydrogenated safflower oil or mixtures thereof. One example of a particularly suitable triacylglycerol-based material for use in making the present candles includes about 50-75 wt. % hydrogenated refined, bleached soybean oil blended with vegetable oil stock having a higher melting point and/or SFI-40. For example, refined, bleached soybean oil may be blended with about 30 to 70 wt. % of the hard fraction obtained by chilling a vegetable oil, such as soybean oil, to 30° F. to 40° F. (about −1° C. to about 5° C.) and separating the solid ("hard fat") and liquid fractions. The resulting blend of the refined, bleached vegetable oil and the hard fat fraction may be hydrogenated to obtain a desired set of physical characteristics, e.g., in terms of melting point, solid fat content and/or Iodine value. The hydrogenation is typically carried out at elevated temperature 400° F. to 450° F. (i.e., about 205° C. to about 230° C. and relatively low hydrogen pressure (e.g., no more than about 25 psi) in the presence of a hydrogenation catalyst, such as a nickel catalyst. One example of a suitable hydrogenation catalyst, is a powdered nickel catalyst provided as a 20-30 wt. % in a solid vegetable oil, such as a hydrogenated soybean oil having an Iodine Value of no more than about 10.

Hydrogenated oil, such as hydrogenated soy oil, is readily commercially available from, for example, food processors like Cargill or Archer Daniels Midland. Alternatively, hydrogenated vegetable oil can be readily made by processes known in the art.

The hydrogenated oil can be used by itself to form various products. For example, if the oil is processed properly, a cosmetic paste or a food container coating wax can be formed. In order to form a food container coating wax, the hydrogenated oil is further processed and deodorized. Processing of the hydrogenated oil which converts the triglycerides into mono- and diglycerides raises the melting point of a vegetable oil only wax. This allows for a food grade coating which should not melt onto the food which is contained therein. Procedures for processing the hydrogenated oil in order to convert triglycerides into mono- and diglycerides are known in the art. Likewise, procedures for bleaching or deoderizing hydrogenated vegetable oils are known in the art.

Other substances can be added to the plant-based wax in order to achieve desired characteristics. In applications which require a harder compound, such as candles, substances such as palmitic acid are added to the hydrogenated oil. The higher the ratio of the hydrogenated oil to the palmitic acid, the softer the product. A higher ratio of palmitic acid produces a harder product. Too high a level of palmitic acid can lead to cracking or breaking. The ratio of the hydrogenated vegetable oil to the palmitic acid can be determined by one of skill in the art. The preferred ratio is approximately 50:50. It is also preferred that the palmitic acid be all natural, plant-based in order to be as environmentally-friendly as the hydrogenated vegetable oil to which it is added. Alternatives to palmitic acid are known in the art.

The physical properties of a triacylglycerol are primarily determined by (i) the chain length of the fatty acyl chains, (ii) the amount and type (cis or trans) of unsaturation present in the fatty acyl chains, and (iii) the distribution of the different fatty acyl chains among the triacylglycerols that make up the fat or oil. Those fats with a high proportion of saturated fatty acids are typically solids at room temperature while triacylglycerols in which unsaturated fatty acyl chains predominate tend to be liquid. Thus, hydrogenation of a triacylglycerol stock ("TAGS") tends to reduce the degree of unsaturation and increase the solid fat content and can be used to convert a liquid oil into a semisolid or solid fat. Hydrogenation, if incomplete, also tends to result in the isomerization of some of the double bonds in the fatty acyl chains from a cis to a trans configuration. By altering the distribution of fatty acyl chains in the triacylglycerol moieties of a fat or oil, e.g., by blending together materials with different fatty acid profiles, changes in the melting, crystallization and fluidity characteristics of a triacylglycerol stock can be achieved.

Herein, when reference is made to the term "triacylglycerol-based material" the intent is to refer to a material made up predominantly of triacylglycerols, typically including at least about 75 wt. % and, preferably about 90 wt. % or more triacylglycerol stock. The triacylglycerol stock, whether altered or not, are generally derived from various plant and animal sources, such as oil seed sources. The terms at least include within their scope: (a) such materials which have not been altered after isolation; (b) materials which have been refined, bleached and/or deodorized after isolation; (c) materials obtained by a process which includes fractionation of a triacylglycerol oil; and, also, (d) oils obtained from plant or animal sources and altered in some manner, for example through partial hydrogenation. Herein, the terms "t riacylglycerols" and "t riglycerides" are intended to be interchangeable. It will be understood that a triacylglycerol oil may include a mixture of triacylglycerols, and a mixture of triacylglycerol isomers. By the term "triacylglycerol isomers," reference is meant to triacylglycerols which, although including the same esterified carboxylic acid residues, may vary with respect to the location of the residues in the triacylglycerol. For example, a triacylglycerol oil such as a vegetable oil stock can include both symmetrical and unsymmetrical isomers of a triacylglycerol molecule which includes two different fatty acyl chains (e.g., includes both stearate and oleate groups).

As indicated above, any given triacylglycerol molecule includes glycerol esterified with three carboxylic acid molecules. Thus, each triacylglycerol includes three fatty acid residues. In general, oils extracted from any given plant or animal source comprise a mixture of triacylglycerols, characteristic of the specific source. The mixture of fatty acids isolated from complete hydrolysis of the triacylglycerols in a specific source is referred to herein as a "fatty acid profile." By the term "fatty acid profile" reference is made to the identifiable fatty acid residues in the various triacylglycerols. The distribution of specific identifiable fatty acids is characterized herein by the amounts of the individual fatty acids as a weight percent of the total mixture of fatty acids obtained from hydrolysis of the particular oil stock. The distribution of fatty acids in a particular oil or fat may be readily determined by methods known to those skilled in the art, such as by gas chromatography.

For example, a typical fatty acid composition of soybean oil ("S BO") is as shown in Table I below.

TABLE 1

Typical SBO Fatty Acid Composition

| Fatty acid | Weight Percent[1] |
|---|---|
| Palmitic acid | 10.5 |
| Stearic acid | 4.5 |
| Oleic acid | 23.0 |
| Linoleic acid | 53.0 |
| Linolenic acid | 7.5 |
| Other | 1.5 |

[1]Weight percent of total fatty acid mixture derived from hydrolysis of soybean oil.

Palmitic acid ("16:0") and stearic acid ("18:0") are saturated fatty acids and triacyiglycerol acyl chains formed by the esterification of either of these acids do not contain any carbon-carbon double bonds. The nomenclature in the above abbreviations refers to the number of total carbon atoms in fatty acid followed by the number of carbon-carbon double bonds in the chain. Many fatty acids such as oleic acid, linoleic acid and linolenic acid are unsaturated, i.e., contain one or more carbon-carbon double bonds. Oleic acid is an 18 carbon fatty acid with a single double bond (i.e., an 18:1 fatty acid), linoleic acid is an 18 carbon fatty acid with two double bonds or points of unsaturation (i.e., an 18:2 fatty acid), and linolenic is an 18 carbon fatty acid with three double bonds (i.e., an 18:3 fatty acid). Palmitic acid is readily commercially available. Food and cosmetic industries use this compound. One example of a supplier of fatty acids, triglycerides, and the like is Witco, Greenwich, Conn.

The fatty acid profile of the triacylglycerol stock which makes up the predominant portion of the present triacylglycerol-based material generally consists predominantly of fatty acids having 18 carbon atoms. The content of shorter chain fatty acids, i.e., fatty acids having 16 carbon atoms or less, in the fatty acid profile of the triacylglycerols is generally no more than about 25 wt. %. Preferably, the triacylglycerol-based material includes at least about 90 wt. % triacylglycerol stock which has a fatty acid profile including no more than about 25 wt. % and, more preferably, no more than about 15 wt. % fatty acids having less than 18 carbon atoms.

As mentioned above, the fatty acid profile of the triacylglycerols commonly predominantly made up of C18 fatty acids. In order to achieve a desirable melting/hardness profile, the C18 fatty acids are typically a mixture of saturated (18:0-stearic acid) and unsaturated fatty acids. The unsaturated fatty acids are predominantly mono-unsaturated fatty acids (18:1), such as oleic acid. Preferably, the triacylglycerols have a fatty acid profile which includes at least about 50 wt. %, more preferably at least about 60 wt. % and, most preferably about 60-70 wt. % 18:1 fatty acid. The fatty acid profile of the triacylglycerols generally includes no more than about 25 wt. % stearic acid. More typically, the fatty acid profile includes about 10 to 20 wt. % and, preferably, no more than about 15 wt. % (18:0 fatty acid).

The triacylglycerols' fatty acid profile is typically selected to provide a triacylglycerol-based material with a melting point of about 40 to 45° C. This can be done by altering several different parameters. As indicated above, the primary factors which influence the solid fat and melting point characteristics of a triacylglycerol are the chain length of the fatty acyl chains, the amount and type of unsaturation present in the fatty acyl chains, and the distribution of the different fatty acyl chains within individual triacylglycerol molecules. The present triacylglycerol-based materials are formed from triacylglycerols with fatty acid profiles dominated by C18 fatty acids (fatty acids with 18 carbon atoms). Triacylglycerols with large amounts of saturated 18 carbon fatty acid (i.e., 18:0 or stearic acid) tend to have melting points and SFI-40s which would be too high for the producing the present candles. The melting point and SFI-40 of such triacylglcerols can be lowered by blending more shorter chain fatty acids and/or unsaturated fatty acids. Since the present triacylglycerol-based materials have fatty acid profiles in which C18 fatty acids predominate, the desired the melting point and/or solid fat index is typically achieved by altering the amount of unsaturated C18 fatty acids present (predominantly 18:1 fatty acid (s)). Preferably, the triacylglycerol-based material is formed from a triacylglycerol stock selected to have a melting point of about 41 to 43° C.

One measure for characterizing the average number of double bonds present in the triacylglycerol molecules of an unsaturated triacylglycerol material is its Iodine Value. The Iodine Value of a triacylglycerol or mixture of triacylglycerols is determined by the Wijs method (A.O.C.S. Cd 1-25). For example, soybean oil typically has an Iodine Value of about 125 to about 135 and a pour point of about 0° C. to about −10° C. Hydrogenation of soybean oil to reduce its Iodine Value to about 90 or less can increase its pour point to about 10 to 20° C. Further hydrogenation can produce a material which is a solid at room temperature and may have a melting point of 60 or even higher. Typically, the present candles are formed from unsaturated triacylglycerol stocks, such as modified vegetable oil stocks, which have an Iodine Value of about 60 to about 75, preferably about 65 to about 71. Particularly, suitable triacylglycerol stocks have an Iodine Value of about 66 to 68.

The method(s) described herein can be used to provide candles from triacylglycerol-based materials having a melting point and/or solid fat content which imparts desirable molding and/or burning characteristics. The solid fat content as determined at one or more temperatures is a measure of the fluidity properties of a triacylglycerol stock. Solid fat content ("SFC") can be determined by Differential Scanning Calorimetry ("DSC") using the methods well known to those skilled in the art. Fats with lower solid fat contents have a lower viscosity, i.e., are more fluid, than their counterparts with high solid fat contents. As used herein, a "plastic fat" is semi-solid to solid, firm but not brittle, easily malleable, with no free oil visible. Plastic fats typically have a solid fat content of no higher than about 20% at 40° C. (104° F.).

The melting characteristics of the triacylglycerol-based material may be controlled based on its solid fat index to provide a material with desirable properties for forming a candle. Although the solid fat index is generally determined by measurement of the solid content of a triacylglycerol material as a function over a range of 5 to 6 temperatures, the triacylglycerol-based materials described herein can be characterized in terms of their solid fat contents at 10° C. ("S FI-10") and/or 40° C. ("SFI-40"). Suitable triacylglycerol-based material for use in making the present candles have a solid fat index exemplified by a solid fat content at 10° C. ("SFI-10") of about 40-60 wt. % and solid fat content at 40° C. ("S FI-40") of about 2-15 wt. %. More typically, the triacylglycerol-based material has an SF-10 of about 57-62 wt. %. The SFI-40 of the triacylglycerol-based material is preferably about 5-15 wt. % and certain particularly suitable embodiments are directed to candles formed from triacylglycerol-based material having an SFI-40 of about 8-12 wt. %.

Feedstocks used to produce the present candle stock material have generally been neutralized and bleached. The triacylglycerol stock may have been processed in other ways prior to use, e.g., via fractionation, hydrogenation, refining, and/or deodorizing. Preferably, the feedstock is a refined, bleached triacylglycerol stock. As described below, the processed feedstock material is often blended with one or more other triacylglycerol feedstocks to produce a material having a desired distribution of fatty acids, in terms of carbon chain length and degree of unsaturation. Typically, the triacylglycerol feedstock material is hydrogenated to reduce the overall degree of unsaturation in the material, e.g. as measured by the Iodine Value, and provide a triacylglycerol material having physical properties which are desirable for a candle-making base material.

It is generally advantageous to minimize the amount of free fatty acid(s) in the triacylglycerol-based material. Since carboxylic acids are commonly somewhat corrosive, the presence of fatty acid(s) in a triacylglycerol-based material can increase its irritancy to skin. The present triacylglycerol-based material generally has an acid value of no more than about 0.1 and, preferably no more than about 0.05. As used herein, the term "acid value" refers to the amount of potassium hydroxide (KOH) in milligrams required to neutralize the fatty acids present in 1.0 gram of triacylglycerol-based material.

The following discussion of the preparation of a vegetable oil derived candle stock material is described as a way of exemplifying a method for producing the present triacylglycerol-based material. A refined, bleached vegetable oil, such as a refined, bleached soybean oil, may be blended with a second oil seed derived material having a higher melting point and/or SFI-40 value. For example, refined bleached soybean oil (circa about 40 to 70 wt. % of the resulting triacylglycerol-based material) can be mixed with 30 to 60 wt. % of the hard fraction obtained by chilling soybean oil at about 38° F. (3-4° C.). The resulting blend would likely still be too soft for use in making a candle. The blend could, however, be hydrogenated until the melting point and/or solid fat index of the material had been modified to fall within a desired range. The final material would then be a partially hydrogenated mixture of a refined bleached vegetable oil and a vegetable oil derived hard fat fraction.

Candles can be produced from the triacylglycerol-based material using a number of different methods. In one, the triacylglycerol-based material is heated to a molten state. The molten triacylglycerol-based material is then solidified around a wick. For example, the molten triacylglycerol-based material can be poured into a mold which includes a wick disposed therein. When the wax of the present invention is used as a candle, the same standard wicks that are used with other waxes can be utilized. In order to fully benefit from the environmentally-safe aspect of the present wax, it is preferred to use braided cotton wick and not a wick with a metal core, such as lead or zinc. The molten triacylglycerol-based material is then cooled to the solidify the triacylglycerol-based material in the shape of the mold. Depending on the type of candle being produced, the candle may be unmolded or used as a candle while still in the mold. Examples of the latter include votive candles and decorative candles, such as those designed to be burned in a clear glass container. If the candle is designed to be used in unmolded form, it may be coated with an outer layer of higher melting point material.

Alternatively, the triacylglycerol-based material can be formed into a desired shape, e.g., by pouring molten triacylglycerol-based material into a mold and removing the shaped material from the mold after it has solidified. A wick may then be inserted into the shaped waxy material using techniques known to those skilled in the art, e.g., using a wicking machine such as a Kurschner wicking machine. In yet another alternative, the triacylglycerol-based material is formed into a plurality of particles ("candle beads") which typically have an average diameter of about 0.1 mm to about 10 mm. In a one embodiment of the invention, the particles are relatively fine, e.g., have an average diameter of about 0.1 mm to about 0.5 mm. The candle beads can be poured into a mold which already includes a wick disposed therein. The wick can then be lit for at least a sufficient amount of time to cause at least an upper layer of the particles of triacylglycerol-based material to aggregate. As used herein, the term "aggregate" means that an interaction between the particles is produced that is sufficient to confer a semi-solid or solid structure to the candle, e.g., through a softening and coalescence of at least the outer surface portions of the individual particles. Preferably, the wick is lit for at least long enough for the upper layer of particles to melt and fuse to form a solid layer ("solidified") of triacylglycerol-based material. The candle beads can also be used to form compression molded candle. See e.g., U.S. Pat. No. 6,019,804, the disclosure of which is herein incorporated by reference, for a description of compression molding of candles.

The particles of waxy material so composed ("candle beads") may exist in a variety of forms, commonly ranging in size from powdered or ground wax particles approximately one-tenth of a millimeter in length or diameter to chips or other pieces of wax approximately two centimeters in length or diameter. Where designed for use in compression molding of candles, the waxy particles are generally spherical, prilled granules having an average mean diameter no greater than one (1) millimeter.

Prilled waxy particles may be formed conventionally, by first melting a triacylglycerol-based material, in a vat or similar vessel and then spraying the molten waxy material through a nozzle into a cooling chamber. The finely dispersed liquid solidifies as it falls through the relatively cooler air in the chamber and forms the prilled granules that, to the naked eye, appear to be spheroids about the size of grains of sand. Once formed, the prilled triacylglycerol-based material can be deposited in a container and, optionally, combined with the coloring agent and/or scenting agent.

The candle beads may be packaged as part of a candle-making kit which includes also typically would include instruction with the candle beads. The candle-making kit typically also includes material which can be used to form a wick.

Other substances, including non-plant substances, may be added to the present invention, though this may compromise the non-toxic character of the preferred embodiment depending on the substance added. For example, the waxes of the present invention may be combined with prior art waxes, e.g., paraffin or beeswax, or with various additives which will alter the characteristics of the wax in a desired manner. Examples of plant-based or non-plant based additives which can be added to the present invention are colors, fragrances, or essential oils.

A wide variety of coloring and scenting agents, well known in the art of candle making, are available for use with waxy materials. Typically, one or more dyes or pigments is employed provide the desired hue to the color agent, and one or more perfumes, fragrances, essences or other aromatic oils is used provide the desired odor to the scenting agent. The coloring and scenting agents generally also include liquid carriers which vary depending upon the type of color- or scent-imparting ingredient employed. The use of liquid organic carriers with coloring and scenting agents is preferred because such carriers are compatible with petroleum-based waxes and related organic materials. As a result, such coloring and scenting agents tend to be readily absorbed into waxy materials. It is especially advantageous if a coloring and/or scenting agent is introduced into the waxy material when it is in the form of prilled granules.

The colorant is an optional ingredient and is commonly made up of one or more pigments and dyes. Colorants are typically added in a quantity of about 0.001-2 wt. % of the waxy base composition. If a pigment is employed, it is typically an organic toner in the form of a fine powder suspended in a liquid medium, such as a mineral oil. It may be advantageous to use a pigment that is in the form of fine particles suspended in a vegetable oil, e.g., an natural oil derived from an oilseed source such as soybean or corn oil. The pigment is typically a finely ground, organic toner so that the wick of a candle formed eventually from pigment-covered wax particles does not clog as the wax is burned. If a dye constituent is utilized, it normally is dissolved in an organic solvent. A variety of pigments and dyes suitable for candle making are listed in U.S. Pat. No. 4,614,625, the disclosure of which is herein incorporated by reference.

A light grade of oil, such as paraffin or mineral oil or preferably a light vegetable oil, serves well as the carrier for the coloring agent when one or more pigments are employed. The preferred carriers for use with organic dyes are organic solvents, such as relatively low molecular weight, aromatic hydrocarbon solvents; e.g. toluene and xylene. The dyes ordinarily form true solutions with their carriers, whereas the pigments, even in finely ground toner forms, are generally in colloidal suspension with in a carrier. Since dyes tend to ionize in solution, they are more readily absorbed into the prilled wax granules, whereas pigment-based coloring agents tend to remain closer to the surface of the wax.

Candles often are designed to appeal to the olfactory as well as the visual sense. This type of candle usually incorporates a fragrance oil in the waxy body material. As the waxy material is melted in a lighted candle, there is a release of the fragrance oil from the liquefied wax pool. The scenting agent may be an air freshener, an insect repellent or more serve more than one of such functions.

The air freshener ingredient commonly is a liquid fragrance comprising one or more volatile organic compounds which are available from perfumery suppliers such IFF, Firmenich Inc., Takasago Inc., Belmay, Noville Inc., Quest Co., and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose and the like.

A wide variety of chemicals are known for perfumery such as aldehydes, ketones, esters, alcohols, terpenes, and the like. A fragrance can be relatively simple in composition, or can be a complex mixture of natural and synthetic chemical components. A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils such as described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like. The scenting agent can also be a liquid formulation containing an insect repellent such as citronellal, or a therapeutic agent such as eucalyptus or menthol. Once the coloring and scenting agents have been formulated, the desired quantities are combined with waxy material which will be used to form the body of the candle. For example, the coloring and/or scenting agents can be added to the waxy materials in the form of prilled wax granules. When both coloring and scenting agents are employed, it is generally preferable to combine the agents together and then add the resulting mixture to the wax. It is also possible, however, to add the agents separately to the waxy material. Having added the agent or agents to the wax, the granules are coated by agitating the wax particles and the coloring and/or scenting agents together. The agitating step commonly consists of tumbling and/or rubbing the particles and agent(s) together. Preferably, the agent or agents are distributed substantially uniformly among the particles of wax, although it is entirely possible, if desired, to have a more random pattern of distribution. The coating step may be accomplished by hand, or with the aid of mechanical tumblers and agitators when relatively large quantities of prilled wax are being colored and/or scented.

Many other additives would be obvious to one of ordinary skill in the art for aesthetic or functional purposes.

In candles, the formulations of the present invention overcome material surface problems such as cracking, air pocket formation, product shrinkage and natural product odor of soybean materials to achieve the final aesthetic and functional product surface and quality demanded by consumers. The invention also overcomes soybean wax performance problems such as optimum flame size, effective wax and wick performance matching for an even burn, maximum soy wax burning time during duration, product color integration and product shelf life. The soybean wax manufacturing and production presents problems such as proper melt temperature for wax liquification and wax product formation, product cure time and the most effective temperatures for cooling/wax curing. Effective methods for material handling and manufacturing procedures appropriate for the demand of working with new soybean materials have been developed in the present invention to address these problems.

The following examples are presented to illustrate the present invention and to assist one of ordinary skill in making and using the same. The examples are not intended in any way to otherwise limit the scope of the invention.

EXAMPLE 1

A triacylglycerol stock suitable for use in making candles can be produced according to the following procedure. A refined, bleached soybean oil (70 wt. %) is blended with a hard fat fraction (30 wt. %) obtained by chilling a deodorized soybean oil at about 38° F. Typical fatty acid profiles for the two starting materials and the resulting blend are shown in Table 2 below. The resulting blend is then hydrogenated at about 420° F. under 15 psi hydrogen in the presence of a nickel catalyst until the resulting triacylglycerol stock has an Iodine Value of 66-69. The hydrogenated product has a melting point of 106-108° F. A typical fatty acid profile for a triacylglycerol stock produced by this process (Formulation I) is shown below in Table 3.

TABLE 2

| | Amount (Wt. %) | | |
|---|---|---|---|
| Fatty Acid(s) | RB-SBO | "Hard Fat" | 70:30 Blend |
| ≦C14 | <0.1 | <0.1 | <0.1 |
| 16:0 | 10-11 | 10-11 | 10-11 |
| 18:0 | 4-6 | 7-9 | 5-7 |
| 18:1 | 20-30 | 45-65 | 30-40 |
| 18:2 | 50-60 | 10-35 | 40-50 |
| 18:3 | 5-10 | 0-3 | 5-10 |
| Other | <1 | <1 | <1 |

TABLE 3

| Fatty Acid(s) | Amount (Wt. %) |
|---|---|
| ≦C14 | <0.1 |
| 16:0 | 10-11 |
| 18:0 | 12-16 |
| 18:1 | 67-70 |
| 18:2 | 4-8 |
| Other | <1 |

The SFI-10 of the hydrogenated soybean oil blend ranges from 43-48 and the SFI-40 ranges from 3-5.

EXAMPLE 2

Hydrogenated soybean oil with the following specifications:

| | |
|---|---|
| Lovibond color red, maximum | 3.00 |
| Free fatty acid, percent maximum | 0.05 |
| Flavor specification | Bland |
| Odor specification | Bland/neutral |
| Peroxide value | 01.00 |
| Iodine Value | 60-72 |
| OSI Stability, hours minimum | 150.00 |
| Wiley Melting Point (° F.) | 104-107 |

-continued

| | |
|---|---|
| Solid Fat Index: | |
| @ 50° F. | 45.0-55.0 |
| @ 70° F. | 30.0-40.00 |
| @ 80° F. | 24.0-34.00 |
| @ 92° F. | 13.0-20.00 |
| @ 104° F. | 3.0-9.00 |
| Fatty Acid Composition: | |
| C16 | 10.4 |
| C18 | 8.4 |
| C18:1 | 77.8 |
| C18:2 | 3.3 |
| C18:3 | 0.1 |
| Bulk Material Storage Temp. (° F.) | 125.0 |

and natural, plant source palmitic acid with the following specifications:

| | |
|---|---|
| Lovibond color red, maximum | 0.10 |
| Lovibond color yellow, maximum | 1.00 |
| Acid value | 203-209 |
| Flavor specification | Bland |
| Odor specification | Bland/neutral |
| Iodine value (maximum) | .08 |
| Titer (° C.) | 55-58 |
| % Un-Sap (Max) | 0.25 |
| % Trans 440/550 nm, Min | 92/98 |
| Carbon Chain Composition: (Saturated) | |
| C14 | 2.0 |
| C16 | 43.0 |
| C18 | 52.8 |
| Bulk Material Storage Temp. (° F.) | 155.0 |

are combined to form Formulation II. The hydrogenated soybean oil is blended with the natural plant source palmitic acid 50%:50% (by weight) and mixed with a power agitator at 200 rpm for 3 minutes. This results in a wax with a wax pour temperature of 150° F. and a wax cure temperature of 72° F.

This formulation provides a wax with surface adhesion properties ideal for use in container candle manufacturing applications. Surface adhesion is important to provide quality container candle products; no air bubbles are formed against the container interior surface, and the wax is held tightly within the container surface, so that it does not slip out.

EXAMPLE 3

Hydrogenated soybean oil with the following specifications:

| | |
|---|---|
| Lovibond color red, maximum | 3.00 |
| Free fatty acid, percent maximum | 0.05 |
| Flavor specification | Bland |
| Odor specification | Bland/neutral |
| Peroxide value | 01.00 |
| Iodine Value | 60-72 |
| OSI Stability, hours minimum | 150.00 |
| Wiley Melting Point (° F.) | 104-107 |
| Solid Fat Index: | |
| @ 50° F. | 45.0-55.0 |
| @ 70° F. | 30.0-40.00 |
| @ 80° F. | 24.0-34.00 |
| @ 92° F. | 13.0-20.00 |
| @ 104° F. | 3.0-9.00 |

-continued

| | |
|---|---|
| Fatty Acid Composition: | |
| C16 | 10.4 |
| C18 | 8.4 |
| C18:1 | 77.8 |
| C18:2 | 3.3 |
| C18:3 | 0.1 |
| Bulk Material Storage Temp. (° F.) | 125.0 |

and a natural, plant source palmitic acid with the following specifications:

| | |
|---|---|
| Lovibond color red, maximum | 0.10 |
| Lovibond color yellow, maximum | 1.00 |
| Acid value | 203-209 |
| Flavor specification | Bland |
| Odor specification | Bland/neutral |
| Iodine value (maximum) | .08 |
| Titer (° C.) | 55-58 {131-136° C.} |
| % Un-Sap (Max) | 0.25 |
| % Trans 440/550 nm, Min | 92/98 |
| Carbon Chain Composition: (Saturated) | |
| C14 | 2.0 |
| C16 | 43.0 |
| C18 | 52.8 |
| Bulk Material Storage Temp. (° F.) | 155.0 {68°F.} |

and a hydrogenated soybean oil with the following specifications:

| | |
|---|---|
| Lovibond color red, maximum | 3.00 |
| Lovibond color yellow, maximum | 10.00 |
| Free fatty acid, percent maximum | 0.05 |
| Flavor specification | Bland |
| Odor specification | Bland/neutral |
| Moisture (% maximum) | 0.05 |
| Soap: PPM max | 3.00 |
| Peroxide value | 01.00 |
| Iodine value | 60-72 |
| OSI Stability, hours minimum | 150.00 |
| Wiley Melting Point (° F.) | 124-127 |
| Fatty Acid Composition: | |
| C14 and lower MAX | 3.0 |
| C16 | 7-14 |
| C18 | 48-57 |
| C18:1 | 30-38 |
| C18:2 (Packed Column) MAX | 3.0 |
| C18:2 (Capillary Column) MAX | 5.0 |
| C18:3 MAX | 1.0 |
| C20 and higher MAX | 5.0 |
| Bulk Material Storage Temp. (° F.) | 165.0 |

were combined to form Formulation III. The first (softer) hydrogenated soybean oil is blended with the natural, plant source palmitic acid and the second (harder) hydrogenated soybean oil in a 7:46:44 weight percent ratio. This mixture is mixed with a power agitator at 250 rpm for 3 minutes. The end formulation has a wax pour temperature of 165° F. and a wax cure temperature of 55° F.

This wax is especially good for use in pillar, votive and taper candles having the opposite surface characteristics of Formulation II. The soybean wax is formulated to inhibit surface adhesion for pillar and votive mold release. Mold release is an important economic consideration in the manufacture of candles, providing for a more rapid turnaround time on production. Effective mold release provides for efficient product manufacturing. This wax was also formulated specifically to integrate natural color additives with an even solid color distribution.

EXAMPLE 4

Hydrogenated soybean oil with the following specifications:

| | |
|---|---|
| Lovibond color red, maximum | 3.00 |
| Free fatty acid, percent maximum | 0.05 |
| Flavor specification | Bland |
| Odor specification | Bland/neutral |
| Peroxide value | 01.00 |
| Iodine Value | 60-72 |
| OSI Stability, hours minimum | 150.00 |
| Wiley Melting Point (° F.) | 104-107 |
| Solid Fat Index: | |
| @ 50° F. | 45.0-55.0 |
| @ 70° F. | 30.0-40.00 |
| @ 80° F. | 24.0-34.00 |
| @ 92° F. | 13.0-20.00 |
| @ 104° F. | 3.0-9.00 |
| Fatty Acid Composition: | |
| C16 | 10.4 |
| C18 | 8.4 |
| C18:1 | 77.8 |
| C18:2 | 3.3 |
| C18:3 | 0.1 |
| Bulk Material Storage Temp. (° F.) | 125.0 |

is used to form Formulation IV. This formulation is 100% hydrogenated soybean oil with minimal fragrance and cosmetic ingredients. The oil, and any additives, are mixed with a power agitator at 200 rpm for 3 minutes creating a product with a wax pour temperature of 150° F. and a wax cure temperature of 72° F.

This is a soy oil based paste ideal for use as a base for hand creams and other cosmetic applications.

EXAMPLE 5

Hydrogenated soybean oil with mono/diglycerides with the following specifications:

| | |
|---|---|
| Lovibond color red, maximum | 3.00 |
| Free fatty acid, percent maximum | 0.1 |
| Flavor specification | Bland |
| Odor specification | Bland/neutral |
| Peroxide value | 05.00 |
| Acid Value MAX | 60-72 |
| Wiley Melting Point (° F.) | 140-145 |
| Bulk Material Storage Temp. (° F.) | 165.0 |

is used to form Formulation V. The hydrogenated soybean oil is treated for conversion of the chains of triglyceride into monoglycerides and diglycerides to achieve a higher melt point and to increase product density/coating effects. The soybean oil is bleached and deodorized by heating the oil to 90° C., adding bleaching clay, heating to 102° C. under vacuum and holding for 30 minutes. This is followed by cooling to 85° C. and then breaking the vacuum with nitrogen. This mixture is processed through a filter press and then subsequently heated to 100° C. for 30 minutes to deareate. The mixture is again nitrogen sparged. The filtered mixture is then heated to 130° C. for one hour with steam sparging at 3.0% (w/w)/hr. This mixture is continued to be heated to 160°

C. and held for an hour. The formulation is then cooled under steam sparging to 130° C., and then nitrogen sparging is begun. This is then cooled under nitrogen sparging to 85° C., and the vacuum is broken with nitrogen.

One of ordinary skill in the art would be able to determine other methods of bleaching and deodorizing the oil.

This coating can be used in a variety of industrial coating applications such as food packaging, release papers for adhesive bandages, release papers for pressure sensitive labels, as coating for wine barrels, bottle caps, as a bottle or jar sealant, or a wine bottling sealant or cork, among many other applications.

EXAMPLE 6

Burn Test

A comparison burn test of votive candles was performed using the wax of the current invention, paraffin wax, and beeswax in identical glass votive containers.

TABLE 4

| Sample materials | | | |
|---|---|---|---|
| | Sample | | |
| | S | P | B |
| Material | Hydrogenated soybean oil wax | 100% paraffin | 100% beeswax |
| Quantity | 3 oz. | 3 oz. | 3 oz. |
| Wick | #CD 10 cotton braid wick | #CD 10 cotton braid wick | #CD 10 cotton braid wick |

The votives were set up in front of 3 identical, standard china plates which served as soot barriers to capture emissions from candle flames during the burn test.

TABLE 5

| Results of burn | | | |
|---|---|---|---|
| Time | Sample | | |
| (hrs.) | S | P | B |
| 0 | Even, steady flame No soot on plate or votive holder | Even, steady flame No soot on plate or votive holder | Even, steady flame No soot on plate or votive holder |
| 2 | Even, steady flame No soot on plate or votive holder | High flame Some soot on plate | Even, steady flame No soot on plate or votive holder |
| 9.5 | Even, steady flame No soot on plate or votive holder | Even, steady flame Increase of soot on plate | Even, steady flame No soot on plate or votive holder |
| 13.25 | Even, steady flame No soot on plate or votive holder | Low flame Extensive soot on plate and votive | Even, steady flame No soot on plate or votive holder |

The flames were extinguished for a period of time and then the samples were relit.

TABLE 6

| Results of continuation burn test | | | |
|---|---|---|---|
| Time | Sample | | |
| (hrs.) | S | P | B |
| 0 | Even, steady flame No soot on plate or votive holder | No flame* Extensive soot on plate and votive, *soot filled wick would not re-ignite | Even, steady flame No soot on plate or votive holder |
| 7 | Even, steady flame No soot on plate or votive holder | | Flame out No soot on plate or glass |
| 10.67 | Even, steady flame No soot on plate or votive holder | | |
| 12.17 | Flame out No soot on plate or votive No waste, wax totally consumed | Soot very visible and measurable at 0.03 g | No soot visible or measurable |

TABLE 7

| Total burn time for the 3 oz. Samples | | |
|---|---|---|
| S | P | B |
| 25.25 hrs. | 13.25 hrs. | 20.33 hrs |

The invention has been described with reference to various specific and illustrative embodiments and techniques. Having described the invention with reference to particular compositions, theories of effectiveness, and the like, it will be apparent to those of skill in the art that it is not intended that the invention be limited by such illustrative embodiments or mechanisms It should be understood that many variations and modifications may be made while remaining within the spirit and scope of the invention.

What is claimed is:

1. A cosmetic paste comprising about 100% by weight hydrogenated vegetable oil wherein the level of hydrogenation is about 60% to about 100%, and wherein the paste has a wax pour temperature of about 150° F.

2. The cosmetic paste of claim 1, wherein the hydrogenated vegetable oil includes hydrogenated soybean oil, hydrogenated cottonseed oil, hydrogenated sunflower oil, hydrogenated canola oil, hydrogenated corn oil, hydrogenated olive oil, hydrogenated peanut oil, hydrogenated safflower oil or a mixture thereof.

3. The cosmetic paste of claim 2, wherein the hydrogenated vegetable oil is hydrogenated soybean oil.

4. The cosmetic paste of claim 1, wherein the hydrogenated vegetable oil comprises a fatty acid profile of no more than about 25 wt. ° A) of C16 or less fatty acids, at least about 50 wt. % of C18:1 fatty acids, and no more than about 20 wt. % C18:0 fatty acids.

5. The cosmetic paste of claim 1, wherein the hydrogenated vegetable oil further comprises a fatty acid profile between about 3 wt. % to about 5 wt. % C18:2 fatty acids, and up to about 1 wt % C18:3 fatty acids.

6. The cosmetic paste of claim 5, wherein the hydrogenated vegetable oil comprises a fatty acid profile of 10 wt. % C16 fatty acids, about 8 wt. % C18 fatty acids, about 77 wt. % C18:1 fatty acids, about 3 wt. % C18:2 fatty acid, and less than about 1 wt. % C18:3 fatty acids.

7. The cosmetic paste of claim 1, wherein the hydrogenated vegetable oil comprises an Iodine Value of about 60 to about 75.

8. The cosmetic paste of claim 7, wherein the hydrogenated vegetable oil comprises an Iodine Value of about 60 to about 72.

9. The cosmetic paste of claim 1, wherein the hydrogenated vegetable oil comprises a melting point of about 104° F. to about 113° F.

10. The cosmetic paste of claim 9, wherein the hydrogenated vegetable oil comprises a melting point of about 104° F. to about 107° F.

11. The cosmetic paste of claim 1, wherein the paste comprises no more than about 0.05% free fatty acid.

12. A cosmetic paste comprising about 100% by weight hydrogenated vegetable oil, wherein the level of hydrogenation is about 60% to about 100%, and wherein the paste has a wax cure temperature of about 72° F.

13. The cosmetic paste of claim 12, wherein the hydrogenated vegetable oil includes hydrogenated soybean oil, hydrogenated cottonseed oil, hydrogenated sunflower oil, hydrogenated canola oil, hydrogenated corn oil, hydrogenated olive oil, hydrogenated peanut oil, hydrogenated safflower oil or a mixture thereof.

14. The cosmetic paste of claim 12, wherein the hydrogenated vegetable oil comprises a fatty acid profile of no more than about 25 wt. ° A) of C16 or less fatty acids, at least about 50 wt. % of C18:1 fatty acids, and no more than about 20 wt. % C18:0 fatty acids.

15. The cosmetic paste of claim 12, wherein the hydrogenated vegetable oil further comprises a fatty acid profile between about 3 wt. % to about 5 wt. % C18:2 fatty acids, and up to about 1 wt % C18:3 fatty acids.

16. The cosmetic paste of claim 12, wherein the hydrogenated vegetable oil comprises an Iodine Value of about 60 to about 75.

17. The cosmetic paste of claim 16, wherein the hydrogenated vegetable oil comprises an Iodine Value of about 60 to about 72.

18. The cosmetic paste of claim 12, wherein the hydrogenated vegetable oil comprises a melting point of about 104° F. to about 113° F.

19. The cosmetic paste of claim 18, wherein the hydrogenated vegetable oil comprises a melting point of about 104° F. to about 107° F.

20. The cosmetic paste of claim 12, wherein the paste comprises no more than about 0.05% free fatty acid.

21. A cosmetic paste comprising 100% by weight hydrogenated vegetable oil wherein the level of hydrogenation is 60% to 100%, and wherein the paste has a solid fat index of 45.0 wt. % to 55.0 wt. % at 50° F., a solid fat index of about 30.0 wt. % to 40.0 wt. % at 70° F., a solid fat index of 24.0 wt. % to 34.0 wt. % at 80° F., a solid fat index of 13.0 wt. % to 20.0 wt. % at 92° F., and a solid fat index of 3.0 wt. % to 9.0 wt.°/0 at 104° F.

22. The cosmetic paste of claim 21, wherein the hydrogenated vegetable oil includes hydrogenated soybean oil, hydrogenated cottonseed oil, hydrogenated sunflower oil, hydrogenated canola oil, hydrogenated corn oil, hydrogenated olive oil, hydrogenated peanut oil, hydrogenated safflower oil or a mixture thereof.

23. The cosmetic paste of claim 22, wherein the hydrogenated vegetable oil is hydrogenated soybean oil.

24. A cosmetic composition comprising the cosmetic paste of claim 1.

25. A cosmetic composition comprising the cosmetic paste of claim 12.

26. A cosmetic composition comprising the cosmetic paste of claim 21.

* * * * *

UNITED STATES PATENT AND TRADEMARK OFFICE

CERTIFICATE OF CORRECTION

PATENT NO. : 8,202,329 B2
APPLICATION NO. : 11/801851
DATED : June 19, 2012
INVENTOR(S) : Timothy A. Murphy et al.

It is certified that error appears in the above-identified patent and that said Letters Patent is hereby corrected as shown below:

On the Title Page:

Item (73), replace "Woodbridge" with --Woodridge--.

In the Claims:

Column 16, claim 4, line 56, before "of C16" replace "25 wt. ° A)" with --25 wt. %--.

Column 17, claim 14, line 27, before "of C16" replace "25 wt. ° A)" with --25 wt. %--.

Column 18, claim 21, line 18, after "to 9.0" replace "wt.°/0" with --wt. %--.

Signed and Sealed this
Fourth Day of September, 2012

David J. Kappos
*Director of the United States Patent and Trademark Office*